United States Patent [19]

McDaniel et al.

[11] Patent Number: 4,501,031

[45] Date of Patent: Feb. 26, 1985

[54] METAL AND PLASTIC COMPOSITE TIBIAL COMPONENT FOR KNEE JOINT

[75] Inventors: John M. McDaniel, Warsaw; Clayton R. Miller, Bremen, both of Ind.

[73] Assignee: Zimmer, Inc., Warsaw, Ind.

[21] Appl. No.: 227,329

[22] Filed: Jan. 22, 1981

[51] Int. Cl.³ .............................................. A61F 1/03
[52] U.S. Cl. ................................ 3/1.911; 128/92 C; 428/164; 428/581
[58] Field of Search ...................... 3/1.9, 1.91, 1.911, 3/1.912, 1.913; 128/92 C, 92 CA, 92 D; 428/164, 581

[56] References Cited

U.S. PATENT DOCUMENTS

| | | | |
|---|---|---|---|
| 3,506,982 | 6/1965 | Steffee | 3/1 |
| 3,790,507 | 2/1974 | Hodosh | 128/92 C X |
| 3,868,730 | 3/1975 | Kaufer et al. | 3/1 |
| 3,953,899 | 5/1976 | Charnley | 128/92 C X |
| 4,016,606 | 4/1977 | Murray et al. | 3/1.911 |
| 4,205,400 | 6/1980 | Shen et al. | 3/1.91 |
| 4,207,627 | 6/1980 | Cloutier | 3/1.911 |
| 4,215,439 | 8/1980 | Gold et al. | 3/1.911 |
| 4,216,549 | 8/1980 | Hillberry et al. | 3/1.911 |
| 4,240,162 | 12/1980 | Devas | 128/92 C X |
| 4,297,993 | 11/1981 | Harle | 128/92 D |

FOREIGN PATENT DOCUMENTS 0014823  1/1980  European Pat. Off. .......... 128/92 D
2247176  3/1974  Fed. Rep. of Germany ... 128/92 D

OTHER PUBLICATIONS

"Plastic is Molded on Metal 'Endoskeleton' to Form Top Half of Ankle Joint," *Materials Engineering*, Nov. 1980, p. 39.
"Multi-Radius TM Total Knee System," ©1980, Zimmer USA, Inc., Brochure B-273-1.
"The GEO-PATELLA TM /GEO-TIBIAL TM Total Knee System," ©1977, Zimmer USA, Inc., Brochure B-263-1.

*Primary Examiner*—Clifford D. Crowder
*Attorney, Agent, or Firm*—Margaret L. Geringer

[57] ABSTRACT

A prosthetic joint component which is comprised of a metal retainer and a plastic bearing portion which is molded integrally onto the top surface of the metal retainer. The metal retainer includes a plurality of notches spaced apart from each other around the periphery of the retainer. The notches enable the plastic, during the molding process, to flow through the notches to create a thickness of plastic completely surrounding the upper surface and the peripheral edge of the retainer (or metal base plate) and terminating in a lower plastic rim surface which is flush with the perimeter of the lower surface of the metal base plate, forming a strong mechanical interlock between the metal and plastic portions of the prosthetic joint component.

6 Claims, 11 Drawing Figures

METAL AND PLASTIC COMPOSITE TIBIAL COMPONENT FOR KNEE JOINT

BACKGROUND OF THE INVENTION

This invention relates generally to the art of orthopaedic prostheses, and more particularly to the type of prosthesis which consists of a supporting metal retainer or base plate portion in conjunction with a plastic bearing portion.

Many types of joint replacement devices involve the use of more than one component. For example, a total knee replacement would involve a femoral and a tibial component. In a typical knee prosthesis, the femoral component is made of metal and the tibial component is made of a plastic, such as ultra high molecular weight polyethylene. Therefore, the contact between the two components is metal to plastic. Since the prosthesis is secured in bone by a grouting agent, such as methyl methacrylate, portions of the plastic component also serve as structural members for anchorage. The plastic material in the tibial component serves as a bearing surface, as well as a structural, load-bearing member.

Clinical experience with such knee joints revealed that in more active patients, mechanical loosening of the tibial component has occurred. Upon examination of the retrieved plastic tibial components, it was discovered that cold flow or creep of the plastic bearing surface has occurred in addition to deformation of the structural portions of the component. Such observations have led to the suspicion that the material properties of plastics may have been exceeded in certain designs.

Plastics belong to the class of viscoelastic materials. These materials tend to deform permanently in time under load, a condition known as creep or cold flow. In addition, the deformation is regional and usually limited to the area where the load is born. Such a behavior can lead to a change of the dimensions of a component which can affect the anchorage of the component in bone. Gross movement of the plastic component in the grout envelope can occur and lead to mechanical loosening of the component. Since the strength of the grouting material is relatively weak, it may also fracture.

In an effort to minimize this problem, certain types of plastic bearing prosthetic components have been reinforced by encasing the plastic in a metal retainer. Such a combination utilizes the plastic as a bearing material and the retainer for structural purposes. When any load is applied to the bearing surface, it is transmitted through the plastic to the metal retainer which distributes it more evenly over the entire prosthesis. Thus, mechanical loosening due to failure of the plastic structure member can be eliminated.

An example of a prior art metal retained tibial component is illustrated in FIGS. 1 and 2. FIG. 1 illustrates the MULTI-RADIUS TM tibial knee component, and FIG. 2 illustrates the supporting metal base plate for this type of tibial component. MULTI-RADIUS is used as a common law trademark of Zimmer USA, Inc. It is noted that in this style of retained knee, the plastic bearing portion is totally supported by the metal retainer. The plastic portion does not extend beyond the peripheral edge of the metal retainer.

Another type of prior art metal retained joint is described in Jean-Marie Cloutier's U.S. Pat. No. 4,207,627. The tibial component of this invention is comprised of a metal tray retainer and two plastic bearing portions which locate into corresponding portions of the metal tray.

Another prior art prosthetic device utilizing a combination of metal and plastic is shown in FIG. 3 and is more fully described in Arthur D. Steffee's U.S. Pat. No. 3,506,982. The device includes a metal anchor 3 fixed into the plastic portion 4. It is noted that in a design such as that shown in the Steffee design where the plastic lips extend substantially beyond the metal anchor, the plastic may deform locally near the anchor. In time, the configuration of the socket 5 may alter and the desired motion of the prosthesis will be lost. If the loading conditions are sufficiently severe, such as that encountered in the knee, (loads up to 3 to 4 times the body weight of the patient), eventual fracture of the plastic component may also result.

OBJECTS OF THE INVENTION

A principle object of this invention is to provide an improved stable construction for implantable prosthetic devices which integrates the rigidity of a metal supporting portion with the antifriction bearing characteristics and chemical inertness of plastics and in which a strong mechanical interlock is formed between the plastic and metal portions.

Another object of the invention is to provide a combination metal/plastic implantable prosthetic device in which the seam between the metal and plastic portions of the device is on the fixation surface of the device, therefore in situations where a grouting agent is used for anchoring the device, the grouting agent seals any exposed seams and thus prevents body fluids from entering into it.

A further object of the invention is to provide a combination metal/plastic implantable prosthetic device in which the plastic extends beyond the peripheral edge of the metal base, and yet not to the extent that loading of the knee joint would cause deformation of the plastic and hence lead to deformation of the bearing surface.

SUMMARY OF THE INVENTION

The present invention accomplishes all of the above objects of invention. The prosthetic joint of this invention is comprised of a metal retainer and a plastic bearing portion which is securely interlocked to the metal retainer or metal base support. The present invention will be described in detail with reference to a knee joint, although it is understood that the principles of the invention are applicable to other joints which could utilize a metal retainer securely affixed to a plastic bearing surface.

The metal retainer or base plate includes a plurality of notches or channel type openings spaced apart around the peripheral edge of the retainer. The peripheral edge of the retainer is comprised of an upper over-hanging edge and a lower undercut ledge. The notches are angled from the top surface of the retainer toward the peripheral edge and angled downward through the over-hanging edge and terminating at the undercut ledge.

The plastic portion is molded integrally onto the metal retainer such that the top surface of the retainer is completely covered with plastic to become the plastic bearing surface of the device. The surface which is to be the bearing surface, is the one which will be referred to as the "top" surface. During the molding process, the plastic flows through the notches and surrounds the upper peripheral edge, as well as flows to the underside of the upper edge (which is the undercut ledge). This creates a strong mechanical interlock of the plastic portion to the metal base support. The thickness of plastic surrounding the undercut peripheral ledge forms a lower plastic rim surface which is flush with the perimeter of the lower surface of the metal retainer at the seam between the metal and plastic portions. The plastic flowing to the undercut in the bottom of the plateau provides retainment around the entire periphery, not just in the area of the notches. The notches permit the plastic to form a rigid, diagonal, gusset type tie-in between the thick plastic on top and the plastic in the undercut.

The plastic portion of the above-described component has therefore extended beyond the metal base to create a seam between the metal and plastic portions which is on the side of the prosthesis which will get anchored to the bone. Hence, if bone cement is utilized, the plastic/metal seam will be sealed from body fluids. Although the plastic is extended beyond the peripheral edge of the metal retainer, it forms only a relatively thin layer of plastic surrounding the periphery of the retainer, such that the lower plastic rim surface is of a substantially less area than the lower metal surface area of the retainer. It is not extended enough to cause deformation of the plastic upon loading of the prosthesis which would be harmful and possibly lead to loosening. The combination of the metal/plastic prosthesis of this invention creates a very stable microinterlock between the metal and plastic portions of the device.

BRIEF DESCRIPTION OF THE DRAWINGS

In order that the principles of the present invention may be readily understood, various examples of the prior art, as well as a particularly advantageous embodiment of the present invention, will be described with reference to the accompanying drawings, which form part of the original disclosure of this application, and wherein.

DETAILED DESCRIPTION OF THE INVENTION

Figure 1:
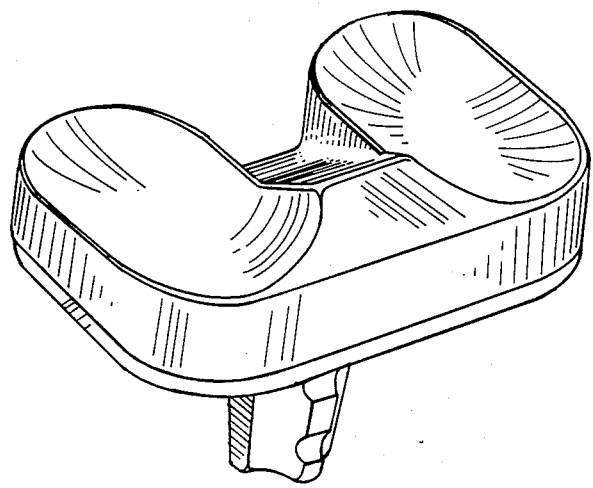
FIG. 1 illustrates a perspective view of the tibial component of a prior art metal-retained knee prosthesis known as the MULTI-RADIUS TM knee.
Figure 2:
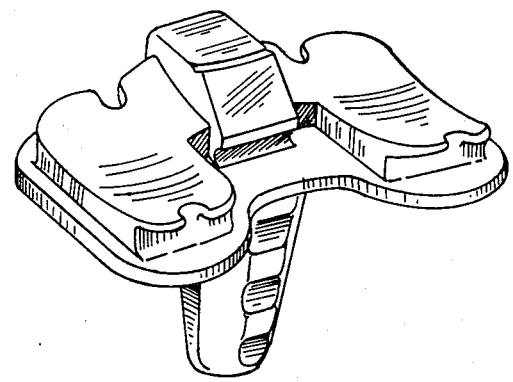
FIG. 2 illustrates a perspective view of the metal base support portion of the tibial component of FIG. 1.
Figure 3:
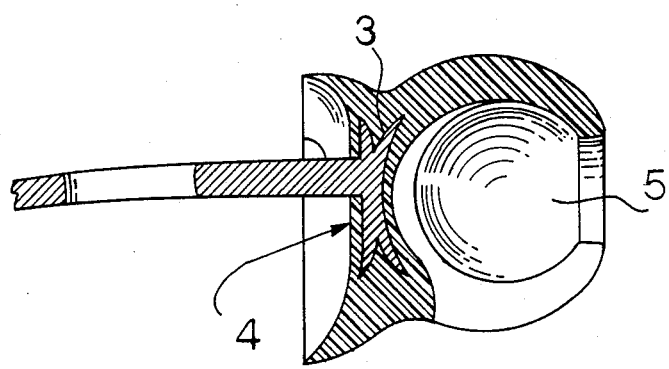
FIG. 3 illustrates a sectional view of the prior art prosthetic device described in U.S. Pat. No. 3,506,982.
Figure 5:
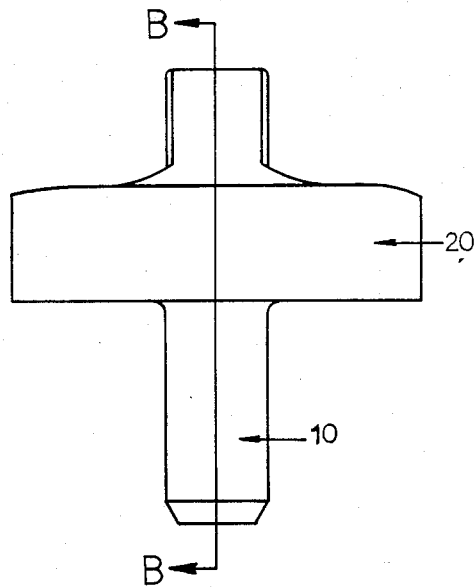
FIG. 5 illustrates a front view of the tibial knee prosthesis of FIG. 4.
Figure 4:
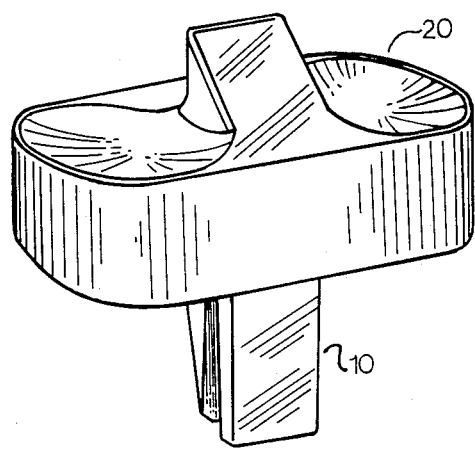
FIG. 4 illustrates a perspective view of a particularly advantageous embodiment of the present invention in the form of a tibial knee prosthesis.

FIGS. 4 through 11 illustrate a particularly advantageous embodiment of the invention. The device of FIG. 4 is a tibial component for a knee prosthesis, and is comprised of a metal base plate 10 (a metal retainer) and a plastic bearing portion 20. It is understood that, although a particular geometry for the bearing portion 20 is illustrated in the FIGS. 4 through 7, any suitable geometry could be used for the bearing portion 20.

The supporting metal base plate 10, shown in FIGS. 8 through 11, is comprised of a lower plate surface 13, an upper plate surface 12, and a peripheral edge 14. In the embodiment illustrated, the lower plate surface includes an anchoring means in the form of a stem 19 which protrudes outwardly from the lower surface 13 of the metal base 10. This is one example of an anchoring means. Standard anchoring means includes many variations of one or more stems (of various configurations) or shorter protruding stubs which are utilized to help firmly anchor a prosthesis in bone. Other anchoring means include various types of texturing, indentations, porous coatings, etc. which are utilized on the surface(s) of the prosthesis which are to be in contact with the bone or which is to be in contact with the grouting material which is used to cement the prosthesis to the bone material.

The peripheral edge 14 is comprised of an upper peripheral edge (overhanging edge) 16, and a lower peripheral edge (undercut ledge) 15. The upper peripheral edge 16 includes a plurality of notches 11 spaced apart from each other around the upper peripheral edge 16. The notches 11 are angled from the upper surface 12 toward the peripheral edge 14 and downward through the overhanging ledge 16. The notches 11 go completely through the overhanging ledge 16 and terminate at the surface of the undercut ledge 15.

Figure 6:
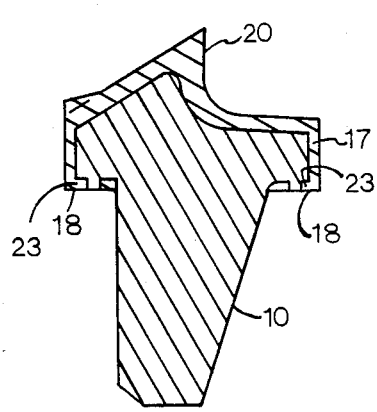
FIG. 6 illustrates a sectional view of the tibial knee prosthesis taken along lines B—B of FIG. 5.
Figure 7:
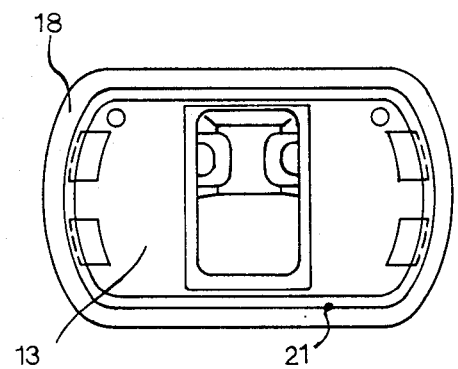
FIG. 7 illustrates a bottom view of the tibial knee prosthesis of FIG. 4.
Figure 9:
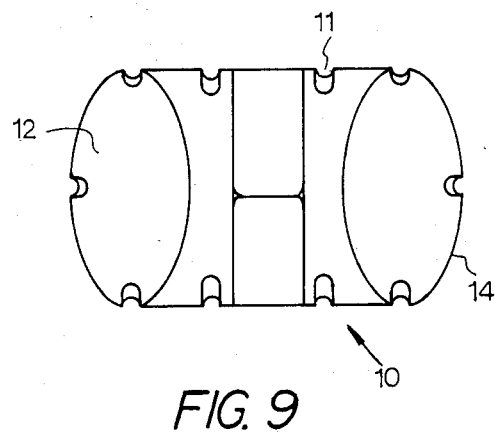
FIG. 9 illustrates a top view of the metal base support portion of FIG. 8.
Figure 8:
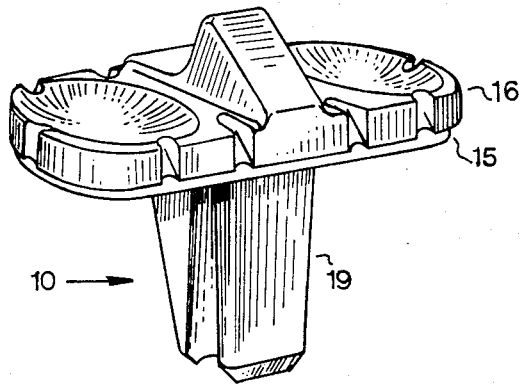
FIG. 8 illustrates a perspective view of the metal base support portion of the tibial knee prosthesis of FIG. 4.
Figure 10:
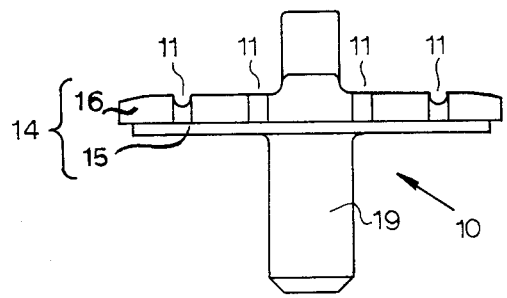
FIG. 10 illustrates a front view of the metal base support of FIG. 8.
Figure 11:
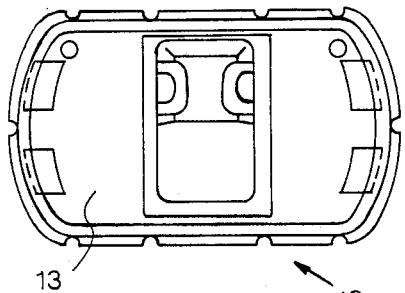
FIG. 11 illustrates a bottom view of the metal base support of FIG. 8.

The plastic bearing portion 20 is molded integrally onto the upper surface 12 of the supporting metal base plate 10. (Surface 12 is identified in FIG. 9). The combined metal and plastic component is illustrated in FIGS. 4 through 7. As shown, the complete upper surface 12 of the base plate 10 is covered with plastic to create the desired bearing surface 22. The plastic also flows through the notches 11 and fills the notches, as well as surrounds the upper peripheral edge 16 and the lower undercut ledge 15. This creates a thickness of plastic 17 (as shown in FIG. 6) which extends beyond the peripheral edge 14 of the metal base plate 10. The thickness of plastic 17 surrounds the upper and lower peripheral edges 15 and 16 and terminates in a lower plastic rim surface 18 which is flush with the perimeter of the lower plate surface 13 at the metal/plastic seam 21 created. The portion of plastic which surrounds the lower undercut peripheral edge 15, forms a plastic lip 23 which extends under the overhanging edge 16. The configuration of the metal retainer 10 described above, in combination with an integrally molded plastic bearing portion 20 creates a metal/plastic prosthesis with a very stable microinterlock between the metal and plastic portions of the device.

It is preferred that the openings created by the notches 11 be no greater than 5 mm in length and 4 mm in width, in order not to affect the elastic modulus of the combination metal plastic component adversely. Any abrupt difference in the elastic modulus of a prosthetic component may result in fracture at the transition point when the component is loaded under use.

In a knee, such as the one illustrated in FIGS. 4-11, the metal base plate of the knee includes a front and back and two relatively shorter sides connecting the front and back. The front and back should each have at least two notches, and each connecting side should have at least one notch. In the embodiment of the knee shown, it is preferred that the notches 11 should be no less than a distance of 6.0 mm apart from each other and no greater than a distance of 25.0 mm apart from each other. This distance is measured from the edge of one notch to the edge of the next notch. In otherwords, this distance is the distance between the notches.

It is also necessary that the amount of plastic which extends beyond the peripheral edge 14 of the metal retainer 10 be relatively thin, such that the lower plastic rim surface 18 is of a substantially less area than the area of the lower metal plate 13 surface. It is preferable that the area of the lower plastic rim surface 18 be no greater than 15% of the area of the lower surface 13 of the metal base support 10. Again, if the thickness of plastic 17 extended too far beyond the periphery of the metal base, it could result in a condition where the plastic could deform and create a condition that would lead to micromovement of the plastic which could lead to loosening of the prosthetic component.

As previously stated, the exposed seam 21 between the plastic and metal portions of the prosthesis is on the surface of the prosthesis which will be anchored to the bone. (In the embodiment described, this surface includes the lower plate surface 13 and the lower plastic rim surface 18.) Therefore, when a grouting material is used to affix the prosthesis to the bone, this seam 21 is buried in the grouting material and hence seals the seam from body fluids.

It is to be noted, as with any metal retained plastic bearing surface, the plastic portion which is above the upper plate surface which is to be the actual bearing surface, should be of a substantial enough thickness so that the plastic will not be in danger of wearing through to the metal.

The combination metal/plastic component of this invention creates a metal/plastic interlock which is mechanically strong. It is understood that the principles of the retainer structure described can be used in combination with a plastic bearing portion for other joint prosthetic components. While this invention has been described and exemplified in terms of a particularly advantageous embodiment, those skilled in the art can appreciate that modifications and variations can be made without departing from the spirit and scope of this invention.

What is claimed is:
1. A load bearing tibial component of a knee prosthesis comprising:
   (a) a supporting metal base plate which is comprised of a lower plate surface, an upper plate surface, and a peripheral edge, the peripheral edge including a plurality of notches spaced apart from each other around the peripheral edge, and;
   (b) a plastic bearing portion which is integrally molded onto the upper surface of the supporting metal base plate, such that the plastic completely covers the upper surface of the metal base to form a desired bearing surface, and wherein the plastic flows through and fills the notches and completely surrounds the peripheral edge to form a thickness of plastic which extends beyond the peripheral edge of the metal base plate, and forming a lower plastic rim surface wherein the area of said lower plastic rim surface is no greater than 15% of the area of the lower surface of the metal base, said lower plastic rim surface being flush with the perimeter of the lower surface of the metal base plate, creating a metal/plastic seam, and wherein the area of the plastic rim is substantially less than the area of the lower metal plate surface, and wherein a secure mechanical interlock is created between the metal plate and plastic portion.

2. A tibial component as described in claim 1 wherein the peripheral edge is comprised of an upper overhanging edge and a lower undercut ledge, and wherein the notches are angled from the upper surface toward the peripheral edge and downward through the overhanging ledge and terminating at the surface of the undercut ledge, and whereby the plastic portion, which completely surrounds the peripheral edge forms a plastic lip due to the plastic surrounding the undercut ledge, and which therefore extends under the over-hanging edge further securing the plastic portion to the metal plate.

3. A tibial component as described in claim 1 or 2 wherein the notches are no greater than 5 mm in length and 3 mm in width.

4. A tibial component as described in claim 1 wherein the lower plate surface includes an anchoring means.

5. A tibial component as described in claim 1 wherein the base plate of the knee includes a front and back and two relatively shorter sides connecting the front and back and wherein, said front and back each have at least two notches and each connecting side has at least one notch.

6. A tibial component as described in claim 1 wherein the notches are no less than a distance of 6.0 mm apart from each other and no greater than a distance of 25.0 mm apart from each other.

* * * * *